United States Patent
Dehmer (10) Patent No.: US 8,257,586 B2
(45) Date of Patent: Sep. 4, 2012

(54) TWO-VALVE ARRANGEMENT FOR LIQUID CHROMATOGRAPHY

(75) Inventor: Bernhard Dehmer, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 390 days.

(21) Appl. No.: 12/667,673

(22) PCT Filed: Jul. 4, 2007

(86) PCT No.: PCT/EP2007/056736
§ 371 (c)(1),
(2), (4) Date: Jan. 4, 2010

(87) PCT Pub. No.: WO2009/003520
PCT Pub. Date: Jan. 8, 2009

(65) Prior Publication Data
US 2010/0187177 A1 Jul. 29, 2010

(51) Int. Cl.
*B01D 15/08* (2006.01)
(52) U.S. Cl. .................. 210/198.2; 210/656
(58) Field of Classification Search .......... 210/635, 210/65, 659, 96.1, 143, 198.2; 96/102
See application file for complete search history.

(56) References Cited

U.S. PATENT DOCUMENTS

| | | | |
|---|---|---|---|
| 4,506,558 A | | 3/1985 | Bakalyar |
| 5,071,547 A | * | 12/1991 | Cazer et al. .............. 210/198.2 |
| 5,468,643 A | * | 11/1995 | Su et al. ................... 436/161 |
| 6,318,157 B1 | * | 11/2001 | Corso et al. .............. 73/61.52 |
| 6,641,783 B1 | | 11/2003 | Pidgeon et al. |
| 2007/0071638 A1 | * | 3/2007 | Kraiczek et al. ........... 422/57 |
| 2010/0101989 A1 | * | 4/2010 | Berndt ....................... 210/188 |

FOREIGN PATENT DOCUMENTS

EP 0022654 A1 1/1981
(Continued)

OTHER PUBLICATIONS

International Search Report dated Feb. 26, 2008.
(Continued)

*Primary Examiner* — Ernest G Therkorn (57) ABSTRACT

A valve arrangement is disclosed for providing a switchable fluid connection between a fluid delivery system for driving a mobile phase and a stationary phase adapted for separating compounds of a sample fluid comprised in the mobile phase. The valve arrangement comprises a first valve comprising a first port adapted to be coupled to the fluid delivery system, a second port, and a third port, wherein the first valve is adapted to switch, in a first switch transition, from a first state wherein the first port is coupled with the second port, over a second state wherein the first port, the second port and the third port are coupled altogether, to a third state wherein the first port is coupled with the third port, a second valve comprising a fifth port adapted to be coupled to the stationary phase, a sixth port, and a seventh port, wherein the second valve is adapted to switch, in a second switch transition from a fourth state wherein the fifth port is coupled with the sixth port, to a fifth state wherein the fifth port is coupled with the seventh port, a first fluid path connecting the second port and the sixth port, and a second fluid path connecting the third port and the seventh port, wherein the second fluid path comprises a sample introduction path adapted for introducing the sample fluid into the mobile phase.

16 Claims, 6 Drawing Sheets

FOREIGN PATENT DOCUMENTS

| | | | |
|---|---|---|---|
| EP | 0309596 | B1 | 4/1989 |
| EP | 0409522 | A | 1/1991 |
| EP | 1688739 | A | 8/2006 |
| EP | 1688739 | A1 | 8/2006 |
| JP | 1996159310 | A | 1/1998 |
| WO | 00/64557 | A | 11/2000 |
| WO | 0064557 | A1 | 11/2000 |
| WO | 02/12878 | A | 2/2002 |
| WO | 0212878 | A1 | 2/2002 |
| WO | 2005/114169 | A | 12/2005 |
| WO | 2005114169 | A1 | 12/2005 |
| WO | 2006/083776 | A | 8/2006 |

OTHER PUBLICATIONS

Written Opinion dated Feb. 26, 2008.
Chinese Office Action for CN Application No. 200780053645.X, mailed on Apr. 27, 2012 (4 pages).

* cited by examiner

TWO-VALVE ARRANGEMENT FOR LIQUID CHROMATOGRAPHY

This application is a 371 and the National Stage of International Application No. PCT/EP2007/056736, filed on 4 Jul. 2007 which designated the United States of America, and which international application was published as Publication No. WO 2009/02530.

The present invention relates to a valve arrangement for a liquid chromatography system.

BACKGROUND ART

In a high performance liquid chromatography (HPLC) system, a fluid has to be provided usually at controlled flow rates (e.g. in the range of microliters to milliliters per minute) and at high pressure (e.g. 100-2000 bar and even beyond).

The fluid, also being referred to as mobile phase, may be pumped by a high pressure pump towards a separation device. Initiated by the high pressure pump, system pressure gradually drops down to atmospheric pressure passing the chain of hydraulic communicating elements (e.g. fluid valves, sample loops, and capillary fluid connections) involved. The predominant pressure drop is expected to be at the separation device, or, in other words, the separation device forms the predominant fluid resistance within the system.

The separation device comprises a material, also being referred to as stationary phase, capable of separating different compounds of a sample being introduced into the mobile phase. Such material, usually so-called beads, which may comprise silica gel, may be filled into a column tube of the separation device that might be coupled to further elements (e.g. a detector and a fraction collector).

A liquid chromatography pumping system is described in EP 0309596 B1 by the same applicant, Agilent Technologies, depicting a pumping apparatus for delivering liquid or fluid at high pressure.

WO/2006/083776 discloses reducing pressure and flow rate variations associated with an actuation of a sample injection valve in liquid chromatography. The sample injection valve comprises a channel having a sufficient length to maintain a continuous flow path from the pump to the column during valve transition.

U.S. Pat. No. 4,506,558 discloses an injection valve for injecting a sample into a chromatography system. The valve comprises two rotor channels proving switchable liquid connections between a pump and a column, and an injection needle and a vent respectively. In addition to the ports connecting the pump, the column, the injection needle and the vent, the stator comprises a channel with interface openings, wherein the interface openings and the rotor channels are arranged such that the pump port is connected to both rotor channels during valve transition. Therewith, an interruption in flow during valve transition is avoided without providing dead space zones or blind volumes, in which a fluid does not flow with the stream.

JP 1996159310 discloses a bidirectional shear valve with a stator having a center through hole and a right and a left through hole with openings along a circle, and a rotor having an arc-line channel having a length for covering simultaneously neighboring two of said openings. Further, bypass channels are associated with two of the through holes so that a fluid communication between the center through hole and either one of the left and right through hole is maintained when rotating the rotor.

EP0022654 discloses a two-valve injection arrangement comprising two sample injection paths, allowing a simultaneous injection of a first sample and a pumping of the mobile phase comprising a second sample towards the stationary phase.

DISCLOSURE

It is an object of the invention to provide an improved valve arrangement for fluid chromatography. The object is solved by the independent claims. Further embodiments are shown by the dependent claims According to embodiments of the present invention, a valve arrangement is described that can e.g. provide a fluid connection between a fluid delivery system (e.g. a fluid pump) and a fluid drain. The fluid delivery system might be adapted for driving a mobile phase towards the fluid drain that might comprise a stationary phase adapted for separating compounds of a sample fluid introduced into the mobile phase. The valve arrangement comprises a first valve and a second valve being fluidly (or fluidically) coupled through two fluid paths, wherein at least one of the paths comprises a sample introduction path adapted for inserting the sample fluid into the mobile phase. The first and second valves are arranged to alternately couple the first fluid path and the second fluid path in-between the fluid delivery system and the stationary phase.

In a further embodiment, the first valve comprises a first switchable fluid path, a first port, a second port, and a third port. The second valve comprises a second switchable fluid path, a fifth port, a sixth port, and a seventh port. The first valve is adapted to switch, in a first switch transition, the first switchable fluid path from a first switching state of coupling the first port with the second port to a third switching state of coupling the first port with the third port, or vice versa. During the first transition, the first port, the second port, and the third port are coupled altogether during an intermediate (second) switching state. The second valve is adapted to switch in a second switch transition the second switchable fluid path from a fourth switching state of coupling the fifth port with the sixth port to a fifth switching state of coupling the fifth port with the seventh port. The first fluid path therein couples the second port with the sixth port, and the second fluid path couples the third port with the seventh port. At least one of the first and second fluid path, e.g. the second path, comprises a sample introduction path.

In operation e.g. in an HPLC system, a sample is inserted into the system in a first phase. The valve arrangement is switched to disconnect the sample introduction path from the fluid delivery system and the stationary phase, so that the sample might be inserted at low pressure. The sample introduction path might comprise a sample loop fully or partially filled with the sample (after sample introduction). In a second phase, the valve arrangement is switched coupling the sample loop in-between the fluid delivery system and the stationary phase to introduce the sample (present in the sample loop) into the mobile phase delivered to the stationary phase at high pressure.

Due to the high pressure in a HPLC system, e.g. in the range between 100 and 2000 bar, e.g. currently 400-1000 bar, fluids have to be regarded as being significantly compressible. If a switching transition connects a low pressurized liquid volume to the high system pressure, the liquid flow will be interrupted to compensate for the compressibility of the low pressurized liquid path. All communicating pressurized liquid within the system and the pump capability for compensation acts as liquid source. Under certain conditions the flow within the separation device may even convert its direction for compensation. This hydraulic dynamic observable in pressure variation or pulsation might lead to damages e.g. in the stationary phase.

According to embodiments of the invention, the valves of the valve arrangement are actuated to alternately subject the first and the second path to pressure (provided by the fluid delivery system) by means of switching the first valve, and to alternately couple the first and the second path to the stationary phase (e.g. column) by means of switching the second valve. The transition of the second valve can be synchronized to the first valve transition such that the second transition is actuated during the second switching state of the first valve, so that each of the first and the second fluid path is already put under pressure before being switched to the stationary phase. Particularly, the sample loop may only be coupled to the stationary phase after being put under pressure before. This can significantly reduce pressure variations due to a change of the sample fluid.

In a further embodiment, during transition of the second valve, the fifth port is either coupled to the sixth port or to the seventh port, without any intermediate switching state (i.e. wherein the fifth, sixth and seventh port are connected altogether). Such transition might be provided such that switching from the sixth to the seventh port is immediately performed. In this case, the column is (virtually) always coupled to the fluid delivery system either over the first fluid path or over the second fluid path. In one embodiment, there is a certain cut-off time provided between such switching. Dependent on the length of the cut-off time, a pressure disturbance, e.g. a pressure loss near to the stationary phase, can be generated. The second valve might be designed such that the cut-off time results into a certain controlled pressure disturbance that might be reliably detected by a detector element. Such pressure disturbance detection might provide an exact starting point of a measurement or exact timing points related to sample changes that might be used to synchronize or identify corresponding measurement results, e.g. for improving a reproducibility of the measurement cycles.

In an embodiment, a further sample introduction path might be inserted into the other (e.g. the first) fluid path, so that each fluid path comprises a respective sample introduction path. Such embodiment allows for a seamless processing of a plurality of sample fluids: while a first sample loop is coupled between the fluid delivery system and the stationary phase to provide a first sample inserted into a first sample loop towards the stationary phase, a second sample loop is decoupled from the fluid delivery system and the stationary phase and coupled to a sample introduction device, e.g. for inserting a second sample fluid. After performing first and second switch transitions, the second sample loop is coupled in-between the fluid delivery system and the stationary phase, while the first sample loop is decoupled from the fluid delivery system and the stationary phase, e.g. for receiving a third sample fluid. A further advantage of this embodiment is that each sample loop or sample introduction path may be put under pressure before being coupled to the stationary phase. Since both sample introduction paths are similar and the valve arrangement is symmetrical with regard to the sample introduction paths, pressure/flow rate variations at the stationary phase might be significantly reduced or even be eliminated, while switching between the sample introduction paths.

Further alternatively, more than two insertion paths can be provided being arranged in parallel and being subsequently switchable in-between the fluid delivery system and the stationary phase.

Alternatively, during the second valve transition, an intermediate (sixth) state can be established, wherein the fifth, sixth and seventh port are coupled altogether. In this embodiment, the fluid delivery system is always fluidly coupled to the stationary phase. However, in a dual sample loop application as described above, such intermediate state might lead an uncertainty in a determination of the analysis start time that might reduce a reproducibility of the measurement cycles.

In a further embodiment, the first valve comprises a first shear valve member with a first interface surface, and a second shear valve member with a second interface surface, whereby the first and second surfaces are rotatably abutting to each other. The first port, the second port, and the third port can be implemented as through holes within the first shear valve member, and the first switchable fluid path can be implemented as a groove within the second surface of the second shear valve member. The switchable fluid path is switched by rotating the shear valve members with respect to each other. One opening of each through hole comprises an interface connectable to the fluid delivery system, the stationary phase or to other HPLC devices, and the other opening interfaces to the second surface comprising the groove. Depending on the rotation position, the groove fluidly interacts with one or a plurality of the ports, so that corresponding flow paths are established through the valve. In an embodiment, the first, second and third port are located circularly, e.g. in an angular distance of each 90 degree. The first fluid path might be implemented in form of a corresponding circular groove covering at least 180 degree, so that the groove has a sufficient length to interact with all three port openings in the intermediate (third) switching state of the first valve.

Correspondingly, the second valve might comprise a third shear valve member and a fourth shear valve member rotatable abutting to each other, wherein the third shear valve members comprises the fifth port, the sixth port, and the seventh port, and the fourth shear valve member comprises the second switchable fluid path.

As the (or each) sample introduction path is coupled between the first and second valves and thus downstream of the first valve, the first valve (in the following also being referred to as eluent distribution valve) only "sees" and supports a flow of the mobile phase before sample introduction and therefore does not get in contact with any sample fluid. Thus, any blind volume (i.e. in which fluid does not flow with the stream, e.g. at the end sections of the first switchable fluid path) within the first valve cannot accumulate any sample fluid, which might lead to contamination or sample cross over likely to distort measurements, e.g. if the sample fluid is changed.

In an embodiment, the first switchable fluid path comprises two end sections each being tapered towards its free ends, and a middle section which might have a constant cross profile between the two end sections. Therewith it is possible to vary the flow restriction while coupling one of the end sections with a corresponding port. This allows for smoothly increasing a fluid pressure of a sample loop after sample introduction and reducing pressure variations at the fluid delivery system.

In an embodiment, the second switchable fluid path of the second valve is implemented as a groove, wherein the third shear valve member further comprises port grooves extending from each the sixth port and the seventh port in direction of the fifth port.

In a further embodiment, the second valve comprises an eighth port adapted to be coupled to an fluid outlet or waste, and a fourth switchable fluid path adapted to switch between coupling the eighth port and the sixth port and coupling the eighth port and the seventh port. The first valve comprises a fourth port adapted to be coupled to a sample syringe or sample pump adapted for driving the insertion of the sample fluid into the mobile phase, and a fourth switchable fluid path adapted to switch between coupling the fourth port and the second port, and coupling the fourth port and the third port. The sample pump might be realized as a metering device adapted for controllable introducing a certain amount of the sample fluid into the mobile phase.

In an embodiment, the valve arrangement is controlled by a valve control unit that controls and synchronizes the first and second valve transitions. Thereby, the valve control unit controls the first valve to perform the first transition from the first switching state, wherein the first port is coupled with the second port, over a second switching state, wherein the first port is coupled with the second port and the third port, to a third switching state, wherein the first port is coupled with the third port. The valve control unit further controls the second valve to perform the second transition from a fourth switching state, wherein the fifth port is coupled with the sixth port, to a fifth switching state, wherein the fifth port is coupled with the seventh port. The first and the second transition might be synchronized such that the second transition is performed during the second switching state of the first valve.

In an embodiment, the first valve and/or the second valve act as check valves for the fluid stream being fluidly connected with the sample pump or metering device. Therein, the first valve or the second valve are moved such a fluid connection between the metering device is alternately switched on and off, while a fluid connection between the fluid delivery system over the other sample introduction path to the separation column is continuously maintained. This can be realized e.g. by providing an overlength of the first switchable fluid path (e.g. forming a circle line segment of more than 90 degree), or by providing port extension grooves extending from each the sixth port and the seventh port in direction of the fifth port of the second valve. While the fluid path is closed by the first or the second valve, the metering device might draw a solvent through the solvent selection valve selectively coupling to one of a plurality of solvents.

The first and third shear valve members might be realized as stator members having a fixed spatial relation to the HPLC system elements. The second and fourth shear valve members might be realized as rotor members arranged to be rotatably moved with respect to each the first and third shear valve member respectively.

In an embodiment the first and the second valve have a common rotational axis. The first and the second valve therein can be arranged as combined unit. In a further embodiment, the first shear valve member (the stator member of the first valve) and the third shear valve member (the stator of the second valve) are formed as common device, and the second shear valve member (the rotor member of the first valve) and the fourth shear valve member (the rotor member of the second valve) are individually rotatable with respect to the common stator around the common axis.

Embodiments of the aforedescribed arrangement may be applied in a liquid separation system comprising a separating device, such as a chromatographic column, having a stationary phase for separating compounds of a sample liquid in a mobile phase. The mobile phase is driven by the pumping apparatus. Such separation system might further comprise at least one of a sampling unit for introducing the sample fluid into the mobile phase, a detector for detecting separated compounds of the sample fluid, a fraction collector for collecting separated compounds of the sample fluid, or any other device or unit applied in such liquid separation systems.

Embodiments of the invention can be partly or entirely embodied or supported by one or more suitable software programs, which can be stored on or otherwise provided by any kind of data carrier, and which might be executed in or by any suitable data processing unit.

DETAILED DESCRIPTION

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

Figure 1:
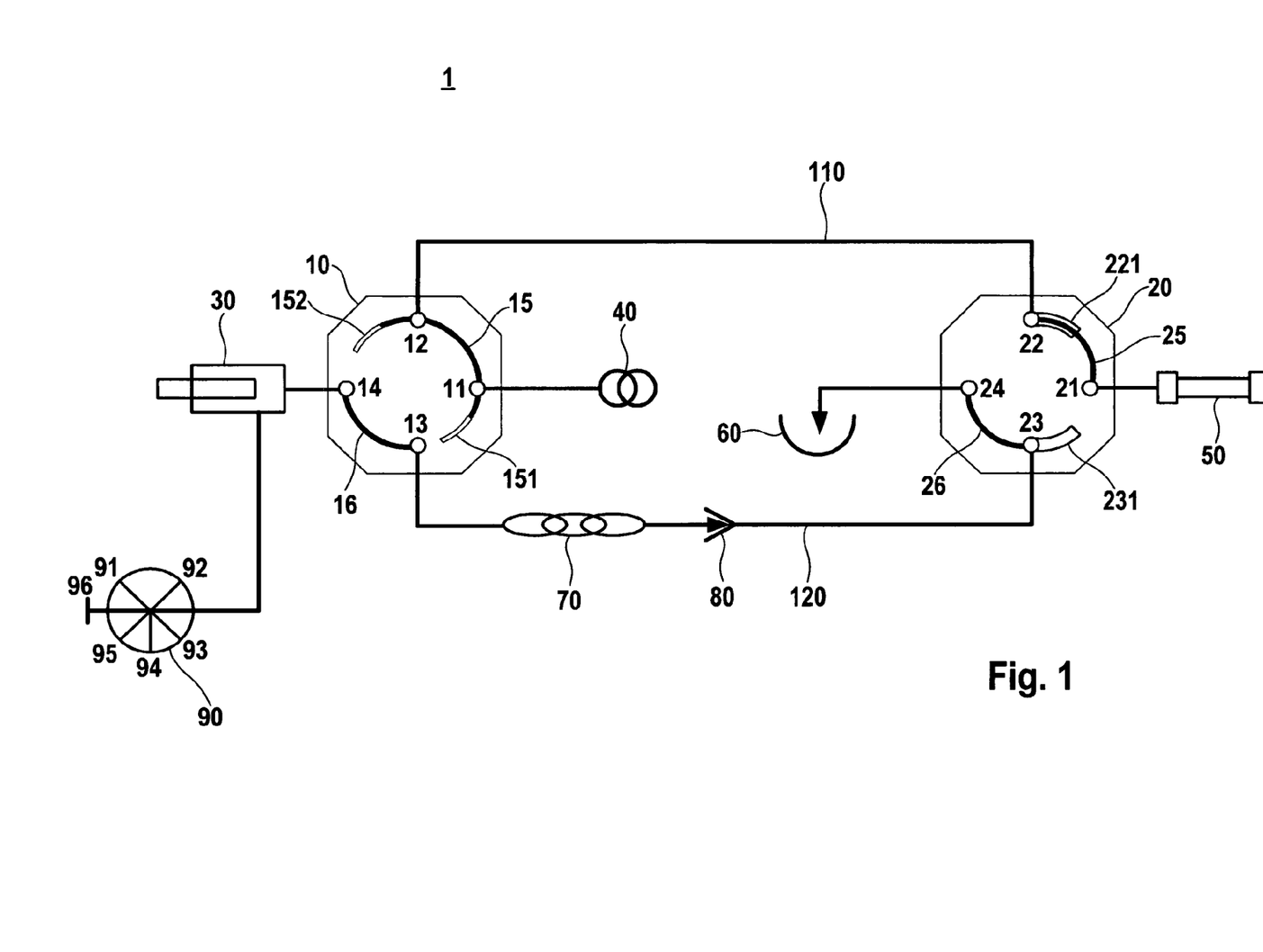
FIG. 1 schematically shows a part of comprising a valve arrangement comprising eluent distribution valve and a sample transfer valve for providing a switchable fluid connection between a fluid delivery system and a column.

Turning to FIG. 1, an exemplary block diagram of a part of an HPLC system is shown comprising a valve arrangement 1, a metering device 30, fluid delivery system or pump 40, a separation column 50, a fluid outlet 60, a sample loop 70, and a needle/seat arrangement 80. The valve arrangement 1 comprises a first valve 10, a second valve 20, a first fluid path 110 and a second fluid path 120. The first valve 10 comprises a first switchable fluid path 15, a third switchable fluid path 16, a first port 11, a second port 12, and a third port 13, and a fourth port 14. The second valve 20 comprises a second switchable fluid path 25, fourth switchable fluid path 26, a fifth port 21, a sixth port 22, a seventh port 23, and an eighth port 24. The first fluid path 110 connects the second port 12 and the sixth port 22, and the second fluid path 120 connects the third port 13 and the seventh port 23. The fourth port 14 is coupled to the metering device 30, and the eighth port 24 is coupled to the fluid outlet 60. The second fluid path 120 comprises a sample introduction path comprising the sample loop 70 and the needle/seat arrangement 80 adapted for introducing a sample fluid into the mobile phase.

Further, FIG. 1 shows a fifth fluid path comprising a third valve or solvent selection valve 90 being coupled to the metering device 30. The solvent selection valve 90 comprises six further ports 91-96, whereof five ports 91-95 are coupled to each a different solvent (not shown here), and a further port 96 is coupled to a closing element. The solvent selection valve 90 is switchable either to selectively couple the metering device to one of the plurality of solvents or to the closing element. It is inherent to the valve arrangement, that the fifth fluid path can never be coupled to the high pressure of pump 40. With respect to the metering device 30 the third switchable fluid path 16 can be switched either connecting the sample loop 70 to the metering device 30 or to close the fifth fluid path without influence on the suited opposite high pressure path. Likewise the fourth switchable fluid path 26 is capable to open and close the low pressurized first 110 or second 120 fluid path without influence on the suited opposite high pressure path. The independent closing conditions of the solvent selection valve 90 and the fluid paths 16 or 26 allows the metering device 30 to work as pump for solvent or sample fluid. While the first and the second valve are switched to decouple e.g. the second fluid path 120 from the pump 40 and the column 50, the metering device is able to draw a selected solvent over the solvent selection valve 90, e.g. for washing the second fluid path after the sample fluid has been delivered to the separation column, as being described in the following in more details.

In the following, the description exemplarily refers to a so-called Split Loop principle of injection which comprises a needle seat arrangement between the first and second valve as shown in FIG. 1. It is understood that the present invention may be used as well with a so-called Fixed Loop principle wherein the injection needle is located fluidly behind the second valve (e.g. being coupled to the eighth port 24 of the second valve.

The fluid delivery system or pump 40 delivers the mobile phase at high pressure, typically at a pressure in the range of 100-2000 bar and even beyond towards the stationary phase. Specifically, the pressure range might be 200-1500 bar, or more specifically 600-1200 bar.

The valves 10 and 20 are by way of example rotary shear valves, each comprising a stator member and a rotor member with adjacent surfaces being rotatable to each other. The valve ports are implemented as passages or through holes through the stator, extending from openings at the stator surface interfacing with the rotor surface to the outside of the stator. At the outside ends, the ports couple with fluid connectors to be coupled to the corresponding HPLC devices. The switchable fluid paths are implemented as grooves within the rotor surface. The rotor can pivot around a center axis being perpendicular to the stator and rotor surfaces. Depending on a rotating position of the rotor member with respect to the stator member, the grooves couple with certain port openings and therewith generate fluid passages between such ports.

The valves 10 and 20 are by way of example 4-port valves. Further, by way of example, the ports are each distributed at equal distances on a circle line, i.e. at angular distances of 90 degree. The switchable fluid paths or grooves 15, 16, 25 and 26 are formed as circle line segments. Therein, the second third and fourth grooves 16, 25 and 26 form quarter circle lines with respect to the rotator surface; differently, the first groove 15 forms a circle line extending over at least 180 degree, so that it has sufficient length to couple the first, second and third port 11, 12 and 13. By way of example, the first groove 15 extends over 205 degree, so that the first groove has a sufficient length to couple all three ports 11, 12, and 13 together during a switching transition of the first valve 10.

The first groove 15 comprises two end sections each tapering towards its free ends and a middle section having a constant cross profile. Being described in more details under FIG. 2, this may allow for smoothly diverting to the second fluid path 120 a small amount of fluid flow to pressurize all fluid paths communicating with the second fluid path within a controllable time Therewith, a variation of the flow rate at the separation column is kept small and thus considerably reducing pressure variations at the fluid delivery system 40 during switching transitions. As flow rate variations might lead to damages at the separation column, e.g. at the stationary phase, reducing a flow rate variation at the column avoids damages to the separation column and thus increases life time of such column as well as repeatability of measurement cycles.

The pump and pump control may be even able to compensate the additional liquid demand without any remarkable pressure or flow variations within the liquid path to the separation device.

The stator member of the second valve further comprises port groves 221, 231 extending form each the sixth port 22 and the seventh port 23 in direction to the fifth port 21. By way of example, the sum of the angles covered by the stator grooves 221 and 231 and the second stator groove 25 is slightly below 180 degree, so that a flow interruption toward the fifth port 21 is implemented while switching the second valve 20. The switching transition behavior of the second valve 20 dependent on the lengths of the port grooves and the switching velocity being described in more details under FIG. 4.

The sample introduction path that is by way of example coupled into the second fluid path 120 is implemented as so-called split loop 70, wherein the needle 80 is adapted to be decoupled from a needle seat to be inserted into a vial (not shown) comprising the sample fluid. In a corresponding sample introduction state, the first valve 10 is switched to couple the metering device 30 over the fourth port 14, the third switchable fluid path 16, the third port 13 and the sample loop 70 to the needle 80. Now, the metering device 30 might suck a controlled amount of sample fluid into the sample loop 70. The sample loop might be partially or completely filled up with the sample fluid. After finishing the sample introduction, the needle 80 is discharged from the vial and positioned into the needle seat in order to provide a fluid coupling between the first valve 10 and the second valve 20 over the sample loop 70. The sample loop might be realized as capillary having an inner diameter of e.g. 0.1-0.5 millimeter. Depending on the length of the capillary, the loop might have a sample fluid volume in a rage between 1 microliter and 1 milliliter.

The first valve 10, in the following also being referred to as eluent distribution valve, only supports the solvent or mobile phase and does not get at any time in contact with the sample fluid inserted in the first or second fluid path. Only the second valve 20, in the following also being referred to as sample transfer valve, receives the sample fluid from the sample loop, to be distributed to the stationary phase. Thus, blind volumes within the first valve 10 in which the fluid does not flow with the stream, cannot accumulate any sample fluid that might distort measurements. Therewith it is possible to provide a switchable groove with an excess length within the first valve that enables reducing pressure variations at the stationary phase, and even a continuous mobile phase flow towards the separation column 50, if the second valve 20 is arranged to provide a continuous flow, too.

Not shown in FIG. 1, the HPLC system might further comprise a detector for detecting separated compounds of the sample fluid and a fraction collector for collecting the separated compounds of sample fluid coupled behind the stationary phase 50.

Figure 2:
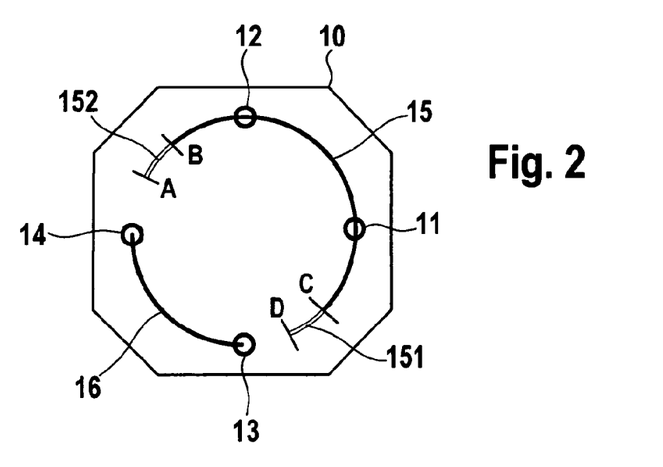
FIG. 2 shows details of the eluent distribution valve.
Figure 3:
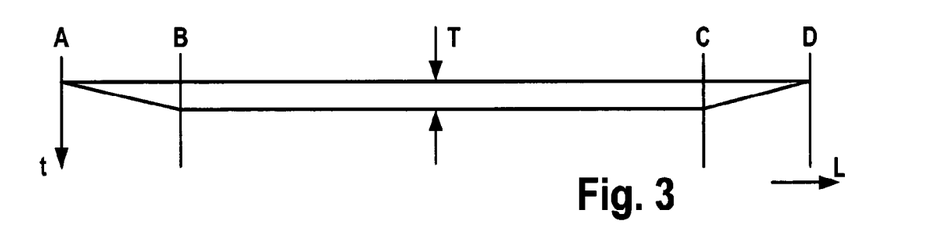
FIG. 3 shows a schematic exemplary profile of a groove comprised by the eluent distribution valve.

FIG. 2 shows aspects of the first valve 10 in more details. The first groove 15, being depicted as a circle line section extending between free end points A and D. The first groove 15 comprises two end sections 151 and 152 each extending between the free end points A and B and inner end points C and D. The middle section of the first groove 15 extending correspondingly between the inner points B and C might form a 180 degree circle line and the end sections 151 and 152 might each cover 15 degree. FIG. 3 shows an exemplary depth profile of the first groove 15 with a groove depth t over the length I. Between first free end point A and first inner end point B, the depth t increases up a maximum depth T. By way of example, as depicted in FIG. 3, the depth increases linearly.

Between the first inner end point B and the second inner end point C, the depth remains constant at the maximum depth T, and between the second inner end point C and the second free end point A, the depth decreases toward the second free end point D. Not shown in FIG. 2, the width of the end sections 151 and 152 might vary, too.

The tapered end sections 151 and 152 allow for varying a flow resistance between the fluid delivery system 40 and the sample loop 70. Thereto, the rotor member of the first valve 10 might be slowly moved between a first position, where a coupling between the first end section 151 and the third port starts, i.e. if turning the rotor member clockwisely, the second free end point D reaches the opening of the third port 13, and a second position wherein the flow resistance remains constant, i.e. if the second inner end point C reaches the opening of the third port 13. This allows for smoothly increasing the fluid pressure onto the sample loop 70 after the sample introduction and thus for reducing pressure variations at the fluid delivery system 40 coupled to the first port 11.

In an embodiment, the movement of the shear valve is controlled in dependency on a fluid parameter, e.g. a pressure or flow rate. In an embodiment, a pressure or flow rate can be measured at the fluid delivery system 40 or at the first port 11 being coupled to the fluid delivery system 40. The movement speed might be varied in dependency on the measured pressure or flow rate. The movement might be temporarily stopped or even reversed (i.e. the direction of the movement is changed in opposite direction), if parameters of the measured value (pressure or flow rate) exceed certain values; e.g. an absolute minimum value and/or a maximum value, a value variation and/or a value gradient (i.e. a derivative of the value over time (e.g. Δp/t)).

Figure 4:
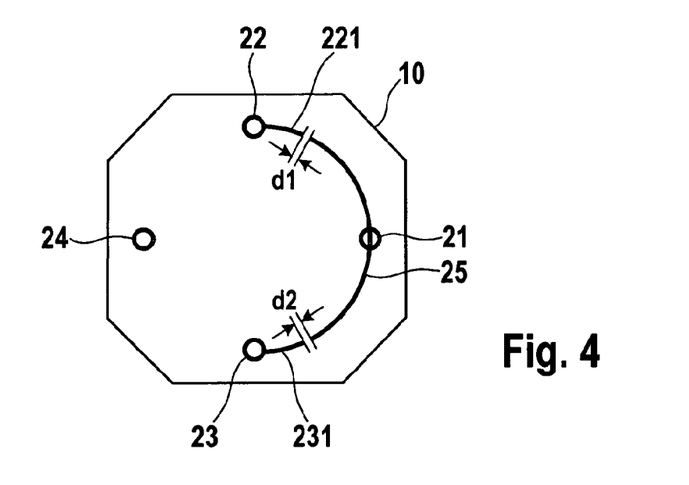
FIG. 4 shows details of the sample transfer valve.

FIG. 4. shows aspects of the second valve 20 in more details. Exemplarily openings of stator port 21-25 are shown equally distributed on a circle line. Further, a first and a second stator groove 221 and 231 extending from the opening of the sixth port 22 and the opening of seventh port 23 respectively in direction of the opening of the fifth port 21 are shown. By way of example the, stator grooves 221 and 231 cover each about 40-50 degree of a circle line, and the second rotor groove 25 covers about 90 degree.

In a first alternative, a sum of the angles covered by the stator grooves and the rotor groove is below the connecting angle between port 22 and port 23, e.g. below 180 degree, if these ports are arranged at 180 degree as shown in FIG. 4. Therein, the stator groove 25 might cover 90 degree, and the stator grooves 221 and 231 might cover less than 45 degree. Correspondingly, the rotor groove 25 never couples to both the first and second stator groove at the same time. At an exemplary position shown in FIG. 4 there is a first gap d1 between the first stator groove 221 and the rotor groove 25 and a second gap d2 between the second stator groove 231 and the rotor groove 25.

While moving the rotor member of the second valve 20 with respect to the stator member from a fourth switching state, wherein the fifth port 21 is coupled to the sixth port 22, to a fifth switching state wherein the fifth port 21 with the seventh port 23, a certain cut-off time depending on the first and second gaps d1 and d2 and the moving speed will occur, wherein the fifth port 21 form both the sixth and the seventh port, and thus from both the first fluid path 110 and the second fluid path 120. Dependent on the length of the cut-off time, a certain amount of a pressure variation (e.g. a pressure loss at the separation column 50 or a pressure increase at the solvent delivery system 40) will occur. The cut-off time might be designed such that a certain pressure loss occurs that is reliably detected by a detector element. Such pressure variation detection might provide an exact starting point of a measurement or exact timing points related to the sample retention time of the separation process. The pressure variation might be chosen to be less than 5% of the system pressure.

In a second alternative, the sum of the angles covered by the stator grooves and the rotor groove equals exactly the connecting angle between port 22 and port 23, e.g. 180 degree, if these ports are arranged at 180 degree as shown in FIG. 4. Therein, the stator grooves 221 and 231 might cover 45 degree, and the rotor groove 25 might cover 90 degree. Correspondingly, the cut-off time is zero, and a flow disruption to the separation column is avoided.

In a third alternative, the sum of the angles covered by the stator grooves and the rotor groove is greater that 180 degree. Therein, the stator grooves 221 and 231 might cover more that 45 degree and the rotor groove 25 might cover 90 degree. In this alternative, the fifth port 21, the sixth 22, and seventh port 23 are coupled altogether in an intermediate switching state. In this alternative, the fluid delivery system is always fluidly coupled to the separation column 50, and both fluid paths are supported in parallel for a short time, as being described in more details under FIG. 6 and FIG. 7 describing dual sample loop applications.

Figure 5:
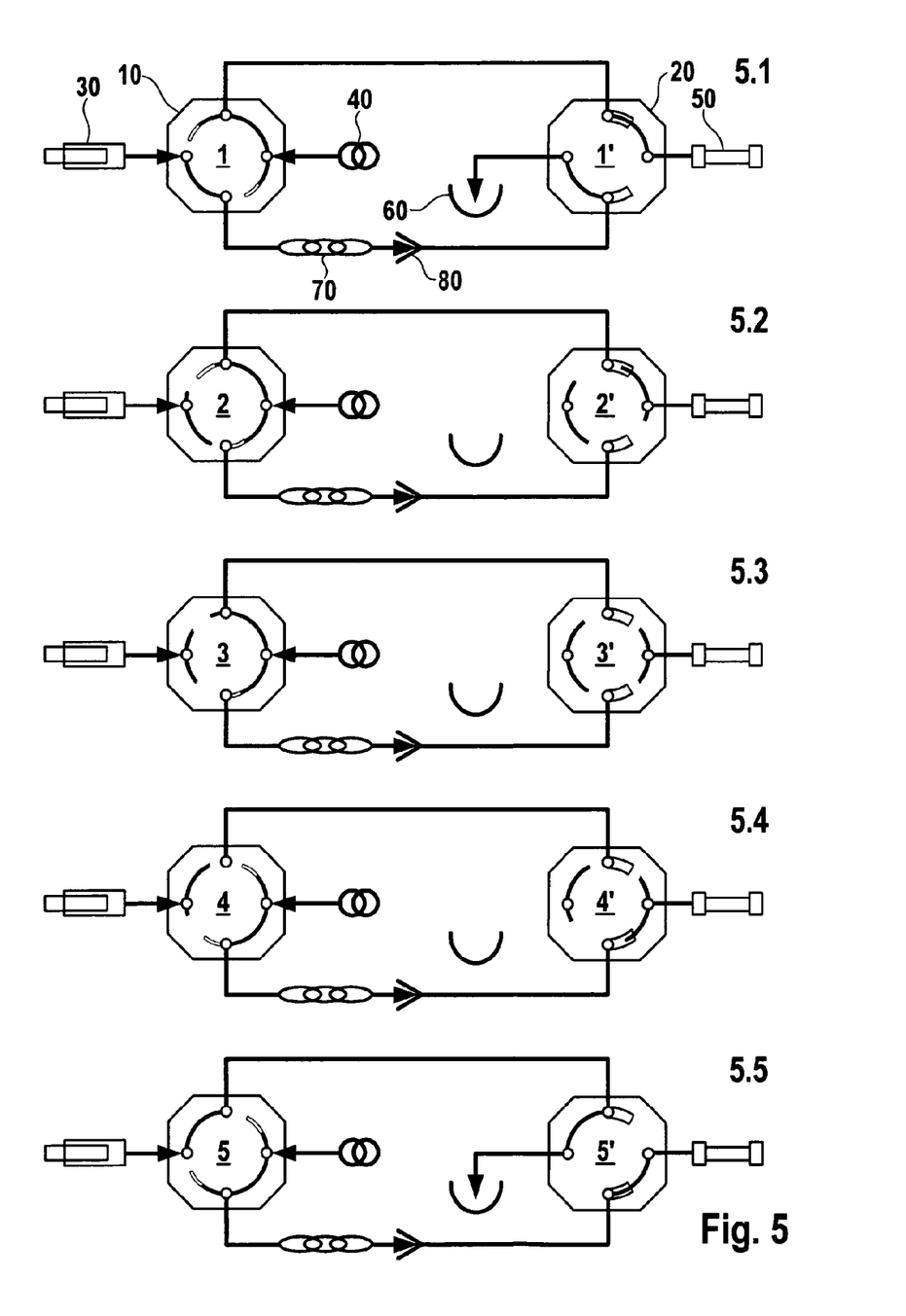
FIG. 5 shows a sequence of switching steps of a first valve arrangement comprising a single sample introduction path.
Figure 6:
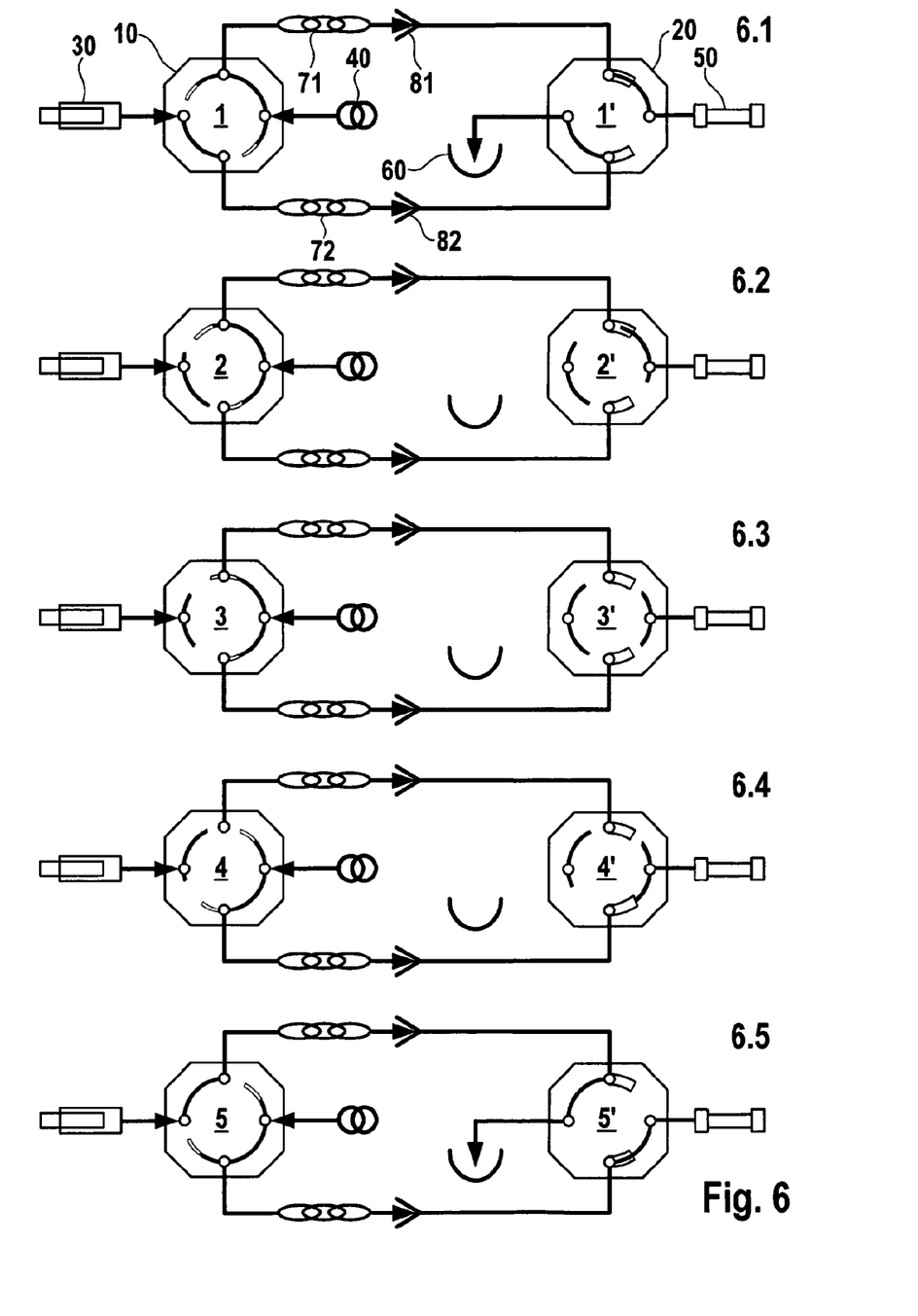
FIG. 6 shows the sequence of switching steps of the first valve arrangement comprising two sample introduction paths.
Figure 7:
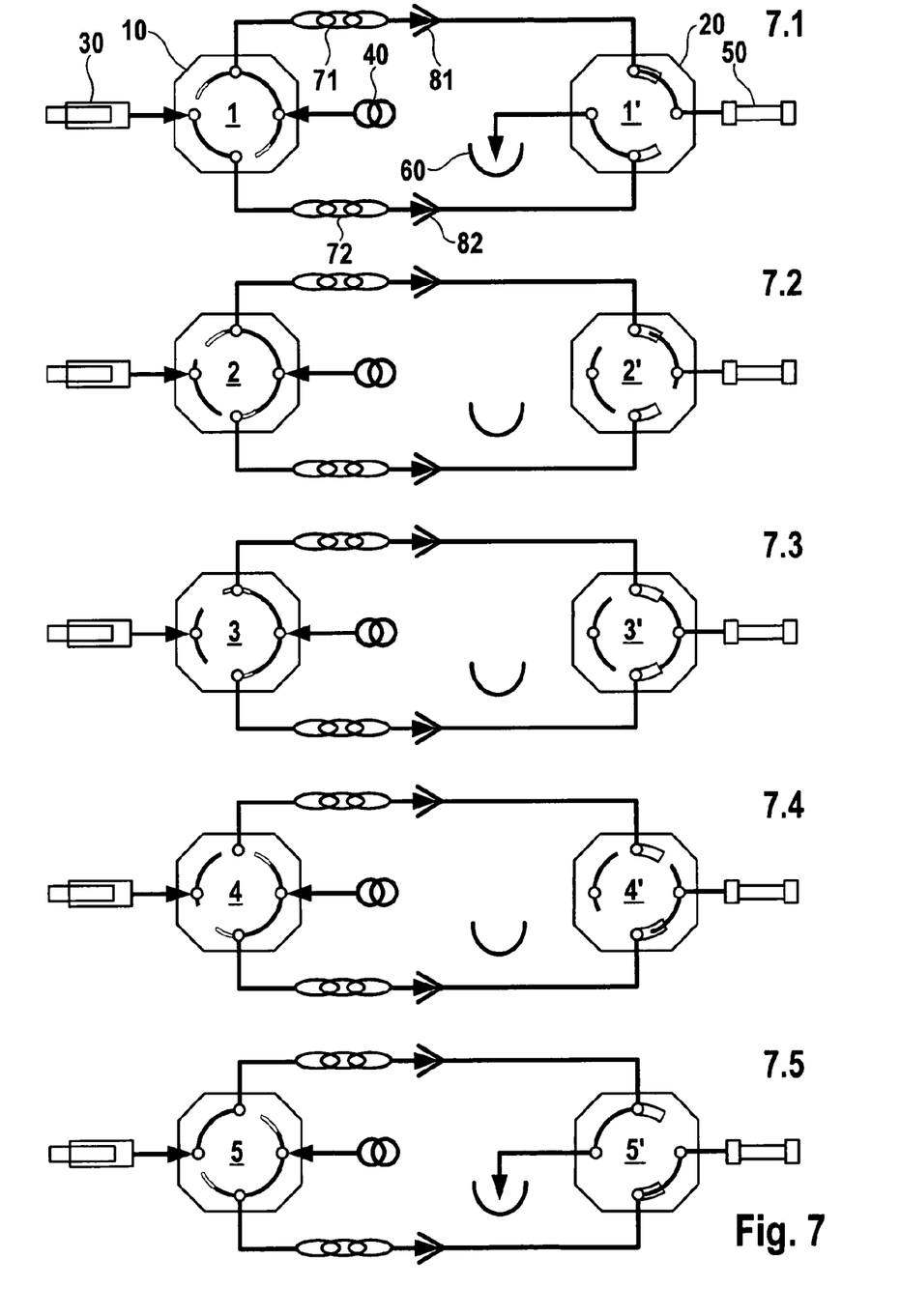
FIG. 7 shows the sequence of switching steps of a second valve arrangement comprising two sample introduction paths.

In the following, three exemplary switching state sequences of three different valve arrangements are described. FIG. 5 shows exemplary switching states of a valve arrangement corresponding to FIG. 1, the valve arrangement having a single sample introduction path comprising a (first) sample loop 70 and a (first) needle arrangement 80. FIG. 6 and FIG. 7 each show similar switching states of alternative valve arrangements, the valve arrangement comprising a first sample introduction path comprising a first sample loop 71 and a first needle arrangement 81 being coupled in-between the second port 12 and the sixth port 22, and a second sample introduction path comprising a second sample loop 72 and a second needle arrangement 82, being coupled in-between the third port 13 and the seventh port 23. The embodiments of FIG. 6 and FIG. 7 differ concerning the angle covered by the stator grooves 221 and 231.

FIG. 5 shows five exemplary switching states or "snap shots" 5.1-5.5 within a sequence of switching steps of the valve arrangement according to FIG. 1. Therein, the (rotor members of) the first and the second valve are both rotated stepwise and clockwise. Such rotations of both valves might be controlled to be carried out synchronously or sequentially, as being described in the following.

The first snap shot 5.1, shows an arbitrary initial step, wherein the first valve is positioned in a first position 1, the first switchable fluid path 15 connecting the first port 11 with the second port 12, and the third path 16 connecting the third port 13 with the fourth port 14. The second valve 20 is positioned to a sixth position 1' the second switchable fluid path 25 connecting the fifth port 21 with the sixth port 22 and the fourth switchable fluid path 26 connecting the seventh port 23 with the eighth port 24. Correspondingly, the fluid delivery system 40 is coupled over the first switchable fluid path 15, the first fluid path 110 and the second fluid path 25 with the separation column 50. Further, the metering device 30 is coupled over the third switchable fluid path 16 to the sample introduction path. The sample loop 70 contains an amount of sample fluid that has been introduced into the sample loop 70 in a previous step.

The second snap shot 5.2 illustrates a state, wherein the second valve moved into a seventh position 2' decoupling the sixth port 23 from the eighth port 24 and thus from the fluid outlet 60, and subsequently, the first valve is moved into a second position 2 so that the third port 13 is decoupled from the third switchable fluid path 16 and coupled to the first switchable fluid path 15 over its tapered end 151. The pressure in the sample loop 70 then rises moderately up to system pressure due to the relatively high fluid resistance of the tapered end. In order to provide a smooth build-up of pressure, the movement of the first valve is carried out sufficiently slow. The movement might even be controlled to be stopped or reversed according to measurements of pressure/flow rate as described above. Such smooth build-up of pressure allows adjusting flow or pressuring variations at the pump 40.

The third snapshot 5.3 illustrates a state, wherein the first valve is moved into a third position 3, wherein the first switchable groove symmetrically couples to the first port 11 to the second and third port 12 and 13, and. the second valve is moved through an eighth position 3', wherein the second switchable fluid path 25 is symmetrically positioned between the sixth port 22 and the seventh port 23, to a ninth position 4'. In the embodiment shown here, the stator grooves 221 and 231 cover less than 45 degree, so that the fifth port 21 is fluidly decoupled from both the sixth port 22 and the seventh port 23. The position shown here corresponds to the exemplary position shown in FIG. 4. In this step, both the first fluid path 110 and the second fluid path 120 are put under pressure.

The fourth snapshot 5.4 illustrates a state, wherein the first valve is moved into a fourth position 4, wherein the first switchable fluid path 15 is decoupled from the second port 12. At the position 4' of the second valve, the first switchable fluid path is decoupled and the complete solvent flow is directed through the second fluid path wherein sixth port 22 and the corresponding stator groove 221 are decoupled from the second switchable fluid path 25.

The fifth snapshot 5.5 illustrates a state, wherein the second valve is moved into a tenth position 5'. The pressure of the decoupled first fluid path releases to the fluid outlet 60. Subsequently, the first valve is moved into a fifth position 5, wherein the third switchable fluid path 16 couples the second port 12 with the fourth port 14.

As stated above, FIG. 6 shows five exemplary states or snap shots 6.1-6.5 that correspond to the snapshots 5.1-5.5 as described under FIG. 5.

The first snapshot 6.1 illustrates a state, wherein corresponding to the first snapshot 5.1 of FIG. 5, the first switchable fluid path 15 connects the first port 11 with the second port 12, the third switchable fluid path 16 connects the third port 13 with the fourth port 14, and the second switchable fluid path 25 connects the fifth port 21 with the sixth port 22 and the fourth switchable fluid path 26 connects the seventh port 23 with the eighth port 24. The fluid delivery system 40 therein is coupled with the separation column 50 over the first sample introduction path (sample loop 71). The first sample fluid inserted into the first sample loop 71 is provided to the separation column 50 under high pressure. Further, the metering device 30 is coupled to the second sample introduction path comprising the second sample loop 72 and the second needle arrangement 82 for inserting a second sample fluid into the second sample loop 72. Before such insertion, the second sample introduction path (sample loop 72 and second needle arrangement 82) might be cleaned up by driving a solvent fluid through said loop to the waste 60 coupled to the eighth port 24.

The second snapshot 6.2 illustrates a state, wherein the third port 13 is decoupled from the third switchable fluid path 16 and coupled to the first switchable fluid path 15. Similarly to step 5.2, the pressure in the second sample loop 72 rises moderately up to system pressure. The first sample loop 71 is still coupled between the fluid delivery system 40 and the separation column 50 delivering the first sample fluid towards the separation column.

The third snap shot 6.3 illustrates a state, wherein the second switchable fluid path 25 is symmetrically positioned between the sixth port 22 and the seventh port 23. Similar to FIG. 5, the stator grooves 221 and 231 cover less than 45 degree while the rotor groove covers 90 degree, so that the fifth port 21 is fluidly decoupled from both the sixth port 22 and the seventh port 23. Both sample introduction paths are coupled to the fluid delivery system and thus put under pressure, but both paths are decoupled from the separation column. Corresponding to the description above, the cut-off time depends on the angular moving speed of the second valve and the angular angle difference between 180 degree and the sum of the angles covered by the each of the rotor grooves and the stator groove.

The fourth snapshot 6.4 illustrates a state, wherein the first switchable fluid path 15 is decoupled from the second port 12 and the sixth port 22 and the corresponding stator groove 221 are decoupled from the second switchable fluid path 25. Therewith, the first sample introduction path is decoupled from both the fluid delivery system and the separation column and the second insertion path is coupled between the fluid delivery system and the separation column to deliver the second sample fluid.

The fifth snapshot 6.5 illustrates a state, wherein the fourth switchable fluid path 26 is coupling the sixth port 22 with the eighth port 24. The pressure of the first sample introduction path releases over the eighth port 24 to the waste. The first sample introduction path might be subsequently cleaned-up up by pumping wash solvent(s) through this path towards the fluid outlet 60 coupled to the eighth port 24 while the third switchable fluid path 16 is coupling the second port 12 with the fourth port 14. The wash solvent might be drawn from one of a plurality of solvent reservoirs being each connected to one of the ports 91-95 of the solvent selection valve 90. Thereto, the solvent selection valve is switched from an "idle position" (port 96) coupling the metering device 30 with the closing member to a selected position (port 91-95) coupling the metering device 30 with the corresponding selected port.

In a further step, the first needle arrangement 71 might be decoupled for drawing a third sample. In further steps not being described in details here, the first and second valve are counter clockwise moved back corresponding to previously described steps in order to again put the first sample introduction path into operation, while decoupling the second sample introduction path from the column.

FIG. 7 shows five exemplary snapshots or states 7.1-7.5 that correspond to the states 6.1-6.5 as described under FIG. 6. FIG. 7 differs from FIG. 6 in that the rotor groove 25 has a sufficient length to simultaneously couple to the sixth port 22 (over the first stator groove 221) and the seventh port 23 (over the second stator groove 231). Accordingly, as indicated in FIG. 7, the stator grooves 221 and 231 by way of example cover more than 45 degree while the rotor groove covers 90 degree.

Correspondingly, in the third snapshot 7.3, while the second switchable fluid path 25 is symmetrically positioned between the sixth port 22 and the seventh port 23, the fifth port 21 is fluidly coupled both to the sixth port 22 and the seventh port 23. In this step, both sample introduction paths are coupled in parallel between the fluid delivery system and the separation column.

The valve arrangement according to embodiments of the invention comprising a eluent distribution valve and a sample transfer valve being separated from each other allows for keeping the eluent distribution valve free from sample fluid. Therewith, it is possible to provide a switchable fluid path within the eluent distribution valve having blind volumes. Such volumes are used according to embodiments to provide the switchable fluid path having a sufficient length to couple three port altogether during a switch transition. If one of said ports is connected to the fluid delivery system, a second fluid paths coupled to another of these ports can be put under pressure while a first fluid pass being coupled to the third of said ports is still under pressure for delivering the mobile phase to the stationary phase. The sample transfer valve can be realized to keep flow variations at an output port being coupled to the stationary phase small or even to avoid such variations without any need to provide blind volumes within the sample transfer valve.

Figure 8:
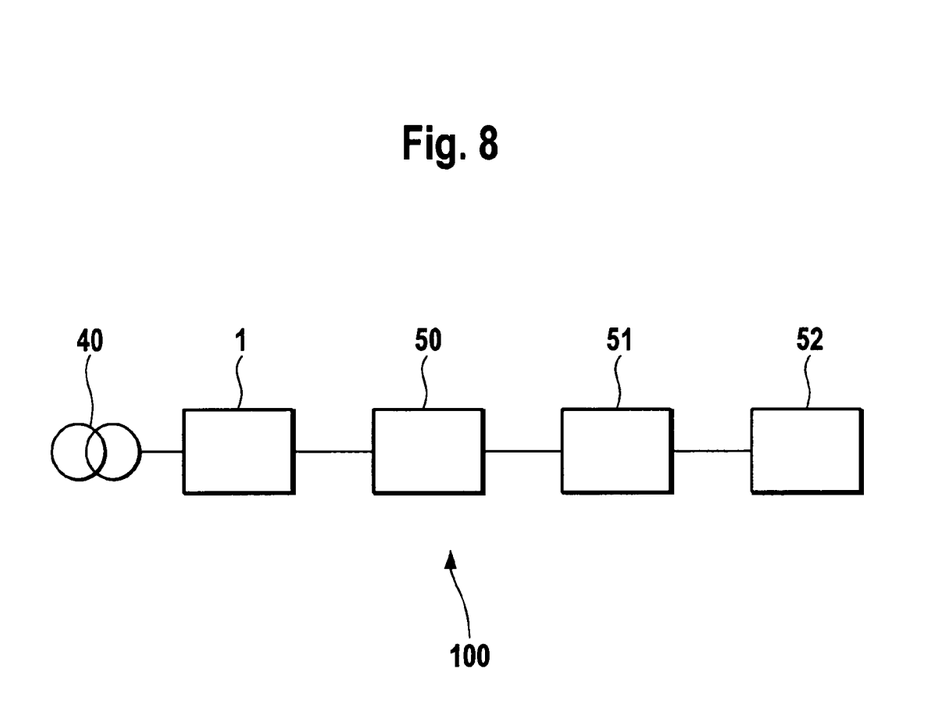
FIG. 8 shows a block diagram of an HPLC system.

FIG. 8 shows a liquid separation system 100. A pump 40 drives a mobile phase through a separating device 50 (such as a chromatographic column) comprising a stationary phase. The valve arrangement 1 as described above is coupled in-between the pump 40 and the separating device 50. The valve arrangement comprises a sample introduction device in order to introduce a sample fluid to the mobile phase. The sample introduction might be realized as fixed loop(s) or split loop(s) as described above. The stationary phase of the separating device 50 is adapted for separating compounds of the sample liquid. A detector 51 is provided for detecting separated compounds of the sample fluid. A fraction collector can be provided for collecting separated compounds of the sample fluid.

Further details of liquid separation system are disclosed with respect to the Agilent 1200 Series Rapid Resolution LC system or the Agilent 1100 HPLC series, both provided by the applicant Agilent Technologies, under www.agilent.com which shall be incorporated herein by reference.

The invention claimed is:

1. A valve arrangement for providing a switchable fluid connection between a fluid delivery system for driving a mobile phase and a stationary phase adapted for separating compounds of a sample fluid comprised in the mobile phase, comprising:
   a first valve comprising a first port adapted to be coupled to the fluid delivery system, a second port, and a third port, wherein the first valve is adapted to switch, in a first switch transition, from a first state wherein the first port is coupled with the second port, over a second state wherein the first port, the second port and the third port are coupled altogether, to a third state wherein the first port is coupled with the third port,
   a second valve comprising a fifth port adapted to be coupled to the stationary phase, a sixth port, and a seventh port, wherein the second valve is adapted to switch, in a second switch transition, from a fourth state wherein the fifth port is coupled with the sixth port, to a fifth state wherein the fifth port is coupled with the seventh port,
   a first fluid path connecting the second port and the sixth port, and
   a second fluid path connecting the third port and the seventh port, wherein the second fluid path comprises a sample introduction path adapted for introducing the sample fluid into the mobile phase.

2. The valve arrangement of claim 1, wherein the fifth port, the sixth port, and the seventh port are coupled altogether within a sixth state being activated during the first switch transition.

3. The valve arrangement of claim 1, wherein the fifth port is decoupled from both the sixth port, and the seventh port within a seventh switching state being activated during the first switch transition.

4. The valve arrangement of claim 1, wherein the first valve comprises a first shear valve member and a second shear valve member rotatable abutting to the first shear valve member, wherein the second shear valve member comprises a first switchable fluid path, and the first shear valve members comprises the first port, the second port and the third port comprising through holes having openings coupling with the first switchable fluid path dependent on a rotatable position of the shear valve member to each other.

5. The valve arrangement of claim 4, wherein the first switchable fluid path has a sufficient length to simultaneously couple with the first port, second port and third port of the first valve during the first switch transition.

6. The valve arrangement of claim 4, wherein the first switchable fluid path comprises two end sections each tapering towards its free ends and a middle section having a constant cross profile connecting each the other ends of the two end sections.

7. The valve arrangement of claim 1, wherein the second valve comprises a third shear valve member and a fourth shear valve member rotatable abutting to the third shear valve member, wherein the fourth shear valve member comprises a second switchable fluid path, and the third shear valve members comprises the fifth port, the sixth port and the seventh port comprising openings coupling with the second switchable fluid path dependent on a rotatable position of the shear valve member to each other.

8. The valve arrangement of claim 7, wherein the second shear valve member further comprises a first and a second port extension groove extending from each the sixth port and the seventh port in direction of the fifth port.

9. The valve arrangement of claim 1, wherein the second valve comprises an eighth port adapted to be coupled to a fluid outlet, and a fourth switchable fluid path adapted to switch between a state wherein the eighth port and the sixth port are coupled together and a state wherein the eighth port and the seventh port are coupled together.

10. The valve arrangement of claim 1, wherein the first valve comprises a fourth port adapted to be coupled to a sample pump for driving the insertion of the sample fluid into the mobile phase, and a fourth switchable fluid path adapted to switch between a state wherein the fourth port and the second port are coupled together, and a state wherein the fourth port and the third port are coupled together.

11. The valve arrangement of claim 10, wherein the sample pump is realized as a metering device adapted for controlling the amount of the sample fluid to be inserted into the mobile phase.

12. The valve arrangement of claim 1, comprising a valve control unit adapted for controlling at least one of: the first switch transition and the second switch transition.

13. The valve arrangement of claim 12, wherein the valve control unit is adapted to receive an information of a property of the mobile phase related to the valve arrangement, and to control said switch transitions in dependency of the received information.

14. The valve arrangement of claim 13, wherein the information of the property of the mobile phase is the fluid pressure or the flow rate at the fluid delivery system, and wherein the valve control unit is adapted for controlling the first switch transition such, that a pressure variation or flow rate variation during the first switching transition is minimized.

15. The valve arrangement of claim 1, being adapted to operate at a fluid pressure within one of the following ranges:
   100-2000 bar, 200-1500 bar, and 600-1200 bar.

16. A high performance liquid chromatography system, comprising:
   the valve arrangement of claim 1,
   a separating device comprising a stationary phase for separating compounds of a sample fluid comprised in a mobile phase, and
   a fluid delivery system adapted for driving a mobile phase through the separating device,
   wherein the first port is coupled to the fluid delivery system, the fifth port is coupled to the separating device.

* * * * *